United States Patent [19]

Tencza

[11] 4,339,428
[45] * Jul. 13, 1982

[54] CAPSULE PRODUCT CONTAINING HIGH DOSAGE OF ASPIRIN IN POWDER OR GRANULATED FORM AND ALKALINE TABLET OR PELLET COMPRISING MAGNESIUM CARBONATE, CALCIUM CARBONATE AND A MAGNESIUM DRY COMPONENT

[75] Inventor: Thomas M. Tencza, Wallington, N.J.
[73] Assignee: Bristol-Myers Company, New York, N.Y.
[*] Notice: The portion of the term of this patent subsequent to Oct. 13, 1998, has been disclaimed.
[21] Appl. No.: 273,015
[22] Filed: Jun. 18, 1981

Related U.S. Application Data

[63] Continuation-in-part of Ser. No. 179,191, Aug. 18, 1980, Pat. No. 4,294,819.
[51] Int. Cl.³ .......................... A61K 9/48; A61K 9/20; A61K 31/60; A61K 33/06
[52] U.S. Cl. .......................... 424/21; 424/16; 424/19; 424/37; 424/154; 424/155; 424/156; 424/157; 424/158; 424/230; 424/235
[58] Field of Search ............ 424/14, 21, 37, 154–158, 424/230, 235

[56] References Cited

U.S. PATENT DOCUMENTS

| | | | |
|---|---|---|---|
| 2,224,256 | 12/1940 | Doushkess | 167/65 |
| 2,447,396 | 8/1948 | Coplans | 167/65 |
| 2,698,332 | 12/1954 | Beekman | 260/448 |
| 2,801,951 | 8/1957 | Cooper | 167/55 |
| 2,888,382 | 5/1959 | Pleyte et al. | 167/82 |
| 2,889,248 | 6/1959 | Paterson | 167/55 |
| 2,918,485 | 12/1959 | Schenck | 260/448 |
| 2,990,328 | 6/1961 | Lincoln | 167/55 |
| 3,019,169 | 1/1962 | Klumpp et al. | 167/82 |
| 3,323,992 | 6/1967 | Schenck | 167/55 |
| 3,608,064 | 9/1971 | Lamb | 424/36 |
| 4,167,558 | 9/1979 | Sheth et al. | 424/22 |
| 4,193,985 | 3/1980 | Bechgaard et al. | 424/19 |
| 4,294,819 | 10/1981 | Tencza | 424/14 |

FOREIGN PATENT DOCUMENTS

| | | | |
|---|---|---|---|
| 593581 | 3/1960 | Canada | 424/230 |
| 808949 | 3/1937 | France | |
| 54675 | 5/1922 | Sweden | 424/230 |
| 754364 | 8/1956 | United Kingdom | 424/230 |
| 827529 | 2/1960 | United Kingdom | 424/230 |
| 1204580 | 9/1970 | United Kingdom | |

OTHER PUBLICATIONS

Bandelin et al., J.A. Ph. A. 19(3):152–153 Mar. 1958 Prac. Phycd., "How Antacid Compounds Influence the Stability of Acetylsalicyclic Acid".
Simon Chem. Abstr. 25, #5932 $^8$ (1931) of J. Lab. Clin. Med. 16:1064–6 (1931), "A Clinical Comparison of Acetylsalicyclic Acid Analgesia With and Without Magnesium Oxide".
Husa et al., J. A. Ph. A. 31:213–216 (1942) 29:78–86, 136–141 (1940), Incompatabilities in Prescriptions III The Use of Inert Powders in Capsules to Prevent Liquefaction Due to Formation of a Eutoctic Mixture IV Deliquescence V to Prevent Liquefaction.
Nozak et al., C.A. 83 #71750u (1975), Effects of Combined Use of Non Steroic Anti-Inflammatory Drugs and Antacids.
Kubo et al., C.A. 60 #375d (1964), Stability of Acetylsalicyclic Acid Compounded with Antacids.
Husa et al., Chem. Abstr. 34 #3444$^{3-7}$ 1940 of J.A. Ph.A. 29:78–86, 136–41 (1940).
Husa et al., Chem. Abstr. 36 #5321$^3$ (1942) of J. A. Ph.A. 31:213–216 (1942).
Conine; J. Pharm. Sci. 54:1580–85, 1965.
A. Baptisti, Arch. int. Pharmacodyn, 1966, 159, No. 1 234–239.

Primary Examiner—Shep K. Rose
Attorney, Agent, or Firm—Irving Holtzman; George A. Mentis

[57] ABSTRACT

A capsule product preferably containing a high dosage of aspirin in powder or granulated form and at least one akaline tablet or pellet; the improvement in which said alkaline tablet or pellet comprises magnesium carbonate, calcium carbonate and a magnesium oxy component such as magnesium oxide, magnesium hydroxide or the combination of magnesium oxide and magnesium hydroxide. The alkaline tablet is preferably dimensioned so that it will contain a maximum amount of material in a minimum volume e.g. a spheroid so that it can be readily dropped into a gelatin capsule e.g. #0 gelatin capsule.

16 Claims, 5 Drawing Figures

4,339,428

CAPSULE PRODUCT CONTAINING HIGH DOSAGE OF ASPIRIN IN POWDER OR GRANULATED FORM AND ALKALINE TABLET OR PELLET COMPRISING MAGNESIUM CARBONATE, CALCIUM CARBONATE AND A MAGNESIUM DRY COMPONENT

RELATED CASES

This application is a continuation-in-part of application Ser. No. 179,191 filed Aug. 18, 1980 now U.S. Pat. No. 4,294,819.

This invention relates to a capsule product containing in combination aspirin preferably at a relatively high dosage level as the significant analgesic ingredient and an alkaline system in tablet or pellet form comprising magnesium oxide, magnesium hydroxide, or a combination of magnesium oxide and magnesium hydroxide, together with magnesium carbonate and calcium carbonate. These capsule products have utility as analgesics and/or antipyretics commonly ascribed to aspirin products. As a matter of convenience, the term "magnesium oxy component" will be used herein and is defined as the group consisting of magnesium oxide, magnesium hydroxide and the combination of magnesium oxide and magnesium hydroxide.

As pointed out in applicant's copending application Ser. No. 179,191 filed Aug. 18, 1980, for a long time it has been appreciated that the coadministration of aspirin along with an alkaline material has certain distinct advantages. One of these is that the presence of the alkaline material serves to increase the rate at which the aspirin is absorbed into the bloodstream. A second benefit is that the alkaline material tends to decrease any irritation to the gastrointestinal musoca that aspirin may cause in some subjects.

Although these are recognized benefits for the coadministration of aspirin and alkaline materials, the incorporation of these materials in a single dosage form has presented problems. Aspirin is hydrolyzed to salicylic acid by alkaline material when moisture is present with the result that some of its effectiveness as an analgesic is reduced. In the case of tabletted products, efforts have been made to stabilize these products by forming the tablets in two layers, one layer containing the aspirin and the other layer containing the alkaline material. This has proven to be relatively successful in providing a stable tablet i.e. one in which the aspirin is not readily hydrolyzed.

In the case of people who have difficulty swallowing tablets, it is also desirable to be able to administer aspirin-containing products in the form of a capsule which is generally considered to be easier to swallow. This is particularly the case when the dosage of aspirin in each dosage form is relatively large. Moreover, aspirin-containing tablets sometimes dissolve in the mouth leaving a taste that most people find objectionable. This is generally avoided when aspirin-containing products are administered in a capsule.

Efforts were made by us to prepare aspirin-containing products commingled with alkaline materials in a capsule to obtain the benefits from this mode of administration. However, when the aspirin and alkaline materials were mixed together in the form of granules or powders and this mix was used to load the capsules, the resulting products did not have the requisite stability due to the presence of moisture and the interaction between the aspirin and the alkaline material.

In the invention described in said application Ser. No. 179,191 there is provided a dosage form of an aspirin product containing alkaline materials which have the requisite stability and speed of reaction with stomach acid. This dosage form is a capsule, either hard or soft shelled, containing the alkaline material which has previously been formed into a small tablet and a granular or powdered mix containing the desired dosage of aspirin. The capsules are produced by filling them first with the tabletted alkaline material, then adding the aspirin composition. In this fashion, the alkaline material is effectively maintained essentially separate from the aspirin-containing material insuring minimal contact between the two. The contact which takes place is only at the surface of the small tablet of alkaline material. This greatly minimizes the changes of any significant hydrolysis of the aspirin by the alkaline material.

When an effort was made to further adapt the teachings in U.S. application Ser. No. 179,191 to an extra strength capsule product containing a relatively high dosage level of aspirin e.g. 500 mg/capsule, certain practical problems were encountered. In scaling up the dosage level of the buffered aspirin products of said U.S. patent application, it is necessary that the ratio of the acid consuming capacity (ACC) of the buffering or alkaline component to aspirin be maintained the same. When the preferred combination of alkaline material disclosed in said application (i.e. the combination of magnesium carbonate and calcium carbonate compressed into a small tablet or pellet) was used in sufficient quantity as to have an ACC adequate for 500 mg of aspirin, the size of the tablet or pellet was too large for the mechanical filling of the tablet or pellet into the capsule.

It has now been found that ACC of the alkaline tablet or pellet can be improved while maintaining the size required for mechanical filling of the tablet or pellet into the capsule if a magnesium oxy component forms part of the alkaline tablet or pellet which also contains magnesium carbonate and calcium carbonate. In a preferred form of this invention, the alkaline mixture is subjected to a granulation step prior to its compression into a tablet or pellet. It has also been found that unexpectedly the rate of reaction of this alkaline mixture with acid, as measured in vitro was surprisingly good.

Although this invention has special application to extra strength analgesic products it is also useful in those cases wherein the aspirin is employed at the ordinary or usual dosage levels.

It is accordingly an object of the present invention to provide a capsule product containing preferably relatively high dosage levels of aspirin and an alkaline tablet comprising a significant amount of a magnesium oxy component as defined herein together with magnesium carbonate and calcium carbonate.

It is also an object of the present invention to provide a process for alleviating pain and/or fever in a subject by administering the dosage form described in the above object.

Other and more detailed objects of this invention will be obvious from the following description and claims.

Figure 3:
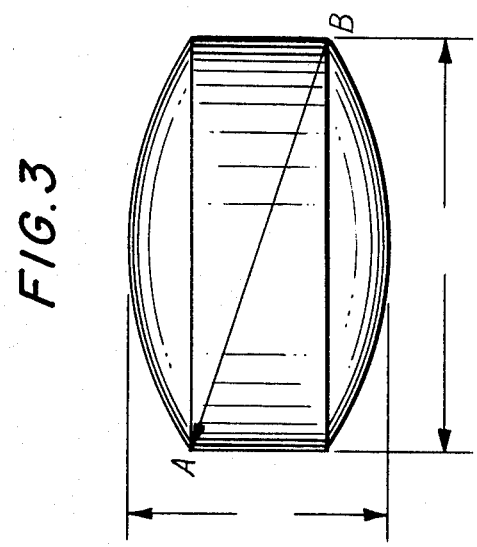
FIG. 3 is a perspective view of an alkaline tablet that may be employed in the present invention.

The present invention provides capsules containing analgesic compositions in which the active analgesic ingredient is normally unstable. Aspirin may be the sole active analgesic ingredient or other non-aspirin active analgesics may be added. Furthermore, other pharmaceutically active ingredients with or without non-aspirin analgesics may also be contained in the capsule.

The small alkaline tablet or tablets which form part of the buffered analgesic product of the present invention will contain a combination of the alkaline materials mentioned above. In addition, however, it may also contain other ingredients described in more detail below which are compatible with the alkaline material in the tablet.

As used herein, the term "aspirin mixture" refers to that powder and/or granular portion of the composition that contains the aspirin but may also contain other compatible powder or granular materials. The term "alkaline tablet" refers to the small tablet which contains the alkaline material but may also contain other compatible ingredients. Unless otherwise specified, percent is given as percent by weight based on the total weight of the product contained in the capsule shell.

Aspirin Mixture

The principal ingredient on a weight basis in the aspirin mixture will usually be aspirin. This will ordinarily take the form of a powder or dry granulation that may vary widely in particle size. In the typical cases, this will usually fall within the range of from about 100% which pass through a 12 mesh screen to about 100% which pass through a 80 mesh screen. A form of aspirin known in the art as "micronized aspirin" may also be employed herein. This is about 325 mesh aspirin and may constitute all or a portion of the aspirin that is included in the products of this invention.

The lower limit of aspirin which will be contained in the capsules of this invention will be about 325 mg with the preferred lower limit being about 400 mg. The upper limit is limited only by the feasibility of swallowing the size of the capsule that is required to contain this material. As a practical matter, this will rarely exceed about 650 mg (10 grains) of aspirin per capsule. In the preferred embodiment, the aspirin level will be about 500 mg/capsule.

The aspirin mixture may also contain conventional excipients which are compatible with aspirin and which are well known to those skilled in the pharmaceutical arts such as, for example, starch, modified starch (e.g. product sold under the trade name "Sta-Rx"), microcrystalline cellulose (Avicel, Ellema), sodium carboxymethyl starch (Explotab, Primojel).

The quantity of excipient in each capsule can vary depending upon the quantity of aspirin contained therein and the size of the capsule. Typically, the quantity of excipient in each capsule is within the range of from about 0% to about 50% by weight based on the weight of the aspirin contained in the mixture.

The aspirin mixture may also contain a lubricant which serves to facilitate the flow of powder or granular materials during filling and processing. There are a number of lubricants well known to those skilled in this art that may be employed. For example, mention may be made of the Silicone Fluids (i.e. polydimethylsiloxane), fumed silicone dioxide (e.g. Cab-O-Sil M-5 or Aerosil 200), light mineral oil, and polyethylene glycol (Carbowax 400).

The quantity of lubricant in the aspirin mixture is related to the quantity of aspirin present. Typically, the quantity of lubricant in each capsule is within the range of from about 0.1% to about 5% by weight based on the weight of the aspirin contained in the mixture.

In addition to aspirin, other pharmaceutically active ingredients may be contained in the aspirin mixture. These may be other analgesics, analgesic potentiators, antihistamines, decongestants, and antitussive agents. By way of illustration of such other pharmaceutically active ingredients, mention may be made of acetaminophen, caffeine, chlorpheniramine maleate, phenylpropanolamine HCl, dextromethorphan, doxylamine succinate, phenindamine tartrate or other phenindamine salts, codeine and surfactants such as sodium lauryl sulfate, polyvinylpyrrolidone, polyoxyethylene (20) sorbitan monooleate (Tween 80), etc.

Alkaline Tablet

The alkaline tablet used in this invention is a small tablet dimensioned so that it can be conveniently dropped into the open end of a capsule which is of a suitable size for use in this invention e.g. #0, #1 and #2. The capsules can be either hard shell or soft shell gelatin capsules, with hard shell preferred. The alkaline tablets will usually comprise the combination of alkaline materials described above that are formed into a granulation by a wet granulation process to provide a material that is readily compressible to form a tablet.

The total quantity of alkaline material as the combination of alkaline ingredients mentioned above may vary somewhat as long as they can be formed into a suitable alkaline sized tablet. The total amount of alkaline material is usually related to the amount of aspirin contained in the aspirin component. Typically, the amount of alkaline material is present in the tablet at a level of from about 20% to about 150% by weight based on the weight of aspirin contained in each capsule.

To get the full benefit of the alkaline component insofar as it has an effect on the absorption rate of the aspirin, it is important that the alkaline tablet have a fast disintegration rate. Good disintegration rates are obtained where the alkaline material consists of a combination of magnesium oxide and/or magnesium hydroxide, magnesium carbonate and calcium carbonate.

The relative quantities of magnesium oxy component, magnesium carbonate and calcium carbonate may vary somewhat. Based on the weight of aspirin contained in each capsule, the following are acceptable ranges: magnesium oxy component from about 2% to about 20%; magnesium carbonate from about 2% to about 10%; and calcium carbonate from about 5% to about 20%. In a preferred aspect of this invention, these percentages are as follows: magnesium oxy component 7.6%; magnesium carbonate 4.8%, and calcium carbonate 19.1%.

The magnesium oxy component may be added to the pre-granulation alkaline mix as magnesium oxide, magnesium hydroxide or as a combination of magnesium oxide and magnesium hydroxide. Since the granulation step involves wetting the pre-granulation mix with water when magnesium oxide is used, some part or all of the magnesium oxide may be converted into magnesium hydroxide.

It is also advantageous to incorporate a disintegrant in the alkaline tablet of the present product to increase the rate at which it disintegrates in the stomach. A variety of materials are known in the tabletting art which will accomplish this function. These include such materials as corn starch, potato starch, wheat starch, modified starch (e.g. Sta-Rx) and sodium carboxymethyl starch (e.g. Primojel). Ordinarily, such materials are present in the alkaline tablet at a level in the range of from about 5% to about 25% by weight based on the total weight of the alkaline tablet.

Other ingredients may be added to the alkaline tablet to improve its physical or organoleptic characteristics or to facilitate the manufacture of the alkaline tablet. Thus, an organic acid e.g. citric acid may be added to improve the hardness of the alkaline tablet to improve the ease of handling. Similarly, a lubricant such as magnesium stearate, stearic acid or silicone fluid may be added to facilitate the tabletting of the alkaline granulation.

The number of alkaline tablets contained in each capsule may vary somewhat. This will ordinarily be related to the quantity of aspirin contained in the capsule and/or the capsule size. For the most part, one or two alkaline tablets will be contained in each capsule although three or more can be employed in unusual circumstances.

Several processes are known to those skilled in this art that may be used in preparing the products of the present invention. In one of the preferred procedures, the alkaline tablet is prepared by first mixing the alkaline ingredient or ingredients with a disintegrant e.g. corn starch until a homogeneous mix is obtained. Alternately, the starch can be added in the form of a 3% to 10% aqueous starch paste. This mix is then moistened by a hot aqueous medium (e.g. deionized water or distilled water). If desired, the organic acid e.g. citric acid may also be added to the solution. The resulting wet mixture is then dried and the dried material is passed through an oscillator provided with appropriate mesh openings or a Tornado Mill to obtain a granulated product. The resulting material is then dried in conventional trays or in a fluid bed drier to a moisture content of 0.5 to 3.0%. The resulting granulation is properly sized and then other excipients such as lubricants and disintegrants are added and this granulation is then pressed into a tablet.

The alkaline tablet is dimensioned so that it will contain a maximum amount of weight of material in a minimum volume so it can be readily dropped into a gelatin capsule e.g. #0 gelatin capsule. This is accomplished by forming the alkaline tablet as a spheroid or near-spheroid having a diagonal dimension of no greater than the diameter of the open end of the capsule. Usually, the diameter of the tablet at its greatest dimension will be in the range of from about 0.210" to about 0.255" for a #0 capsule. For different sized capsules, the appropriate diameter tablet will be used and varies depending on size of the capsule and the amount of aspirin used.

Because of the difficulty in compressing a granulation into a true spheroidal tablet in the preferred practice of this invention, a modified deep ball punch is employed.

Figure 2:
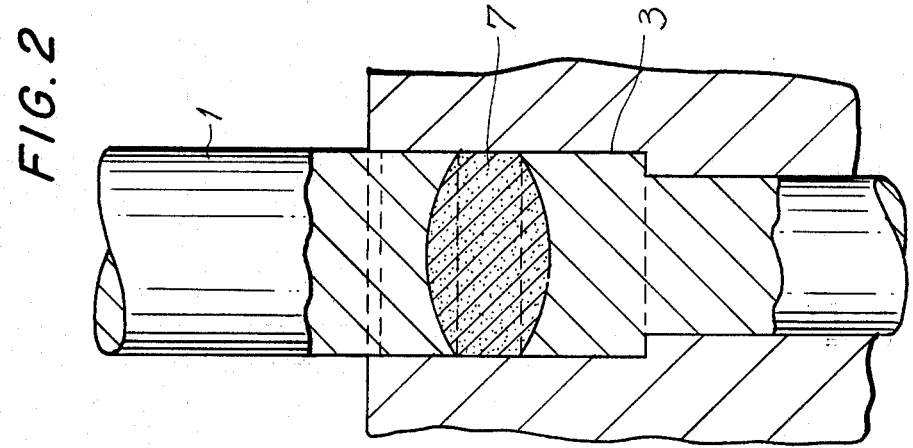
FIG. 2 is a view, similar to that shown in FIG. 1, showing the tablet punch and mold when they are brought together.
Figure 1:
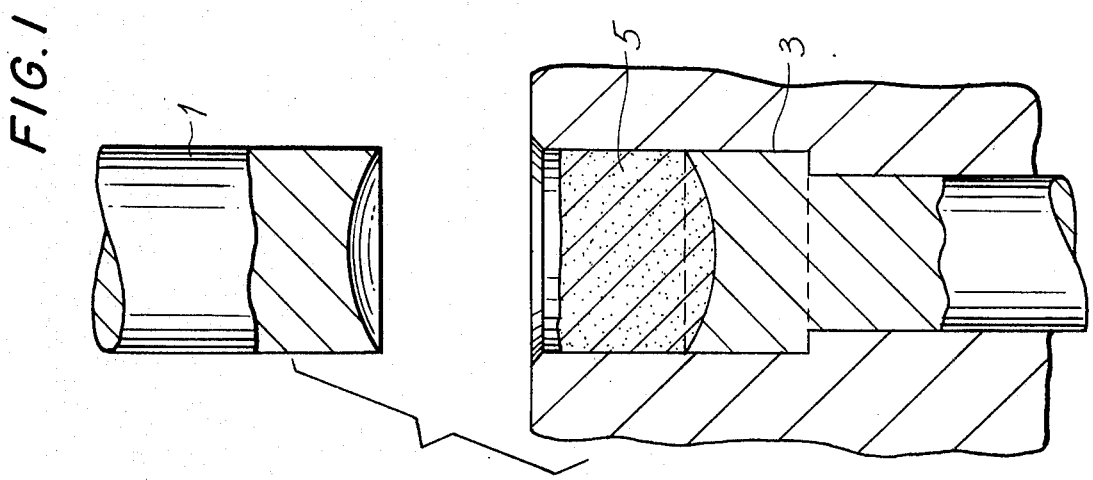
FIG. 1 is a view, partly in section of a tablet punch and mold that may be employed in shaping the alkaline tablet or pellet employed in the present invention, showing the position of these elements before they are brought together.

A suitable punch is illustrated in FIGS. 1 and 2. In FIG. 1, the punch is shown at 1 and the mold is shown at 3. The alkaline mix 5 is placed in the mold 3 and then punch 1 is brought down to compress alkaline mix 5 into tablet or pellet 7. This gives a modified spheroidal tablet having the form of a solid cylinder provided with an upper and lower dome (see FIG. 3). In this case, the important dimension is the diameter of the tablet in longitudinal cross section that extends from the top of one vertical side to the bottom of the other vertical side (see diameter A–B in FIG. 3). A suitable diameter is in the range of from about 0.210" to about 0.245".

Figure 4:
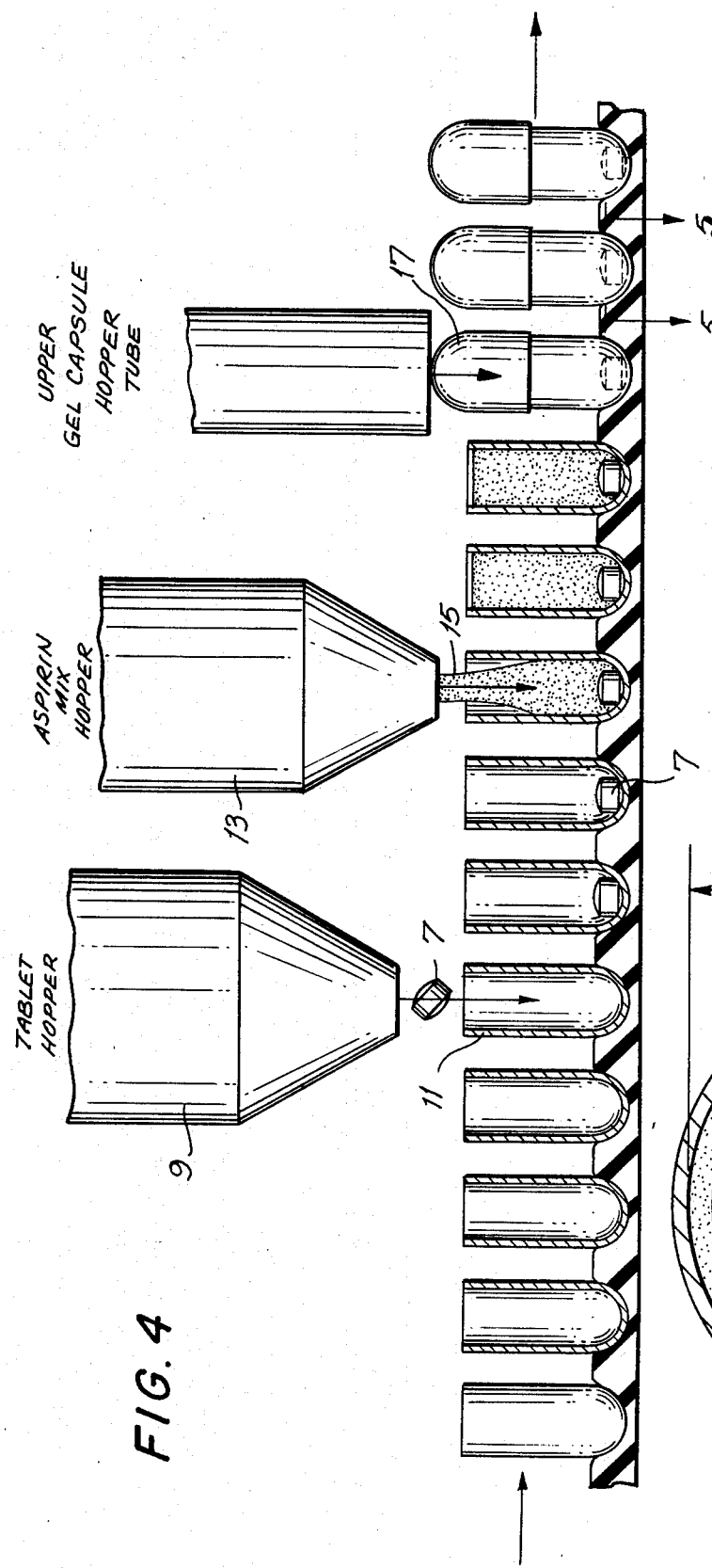
FIG. 4 is a schematic view of an assembly line for assembling the products of the present invention.
Figure 5:
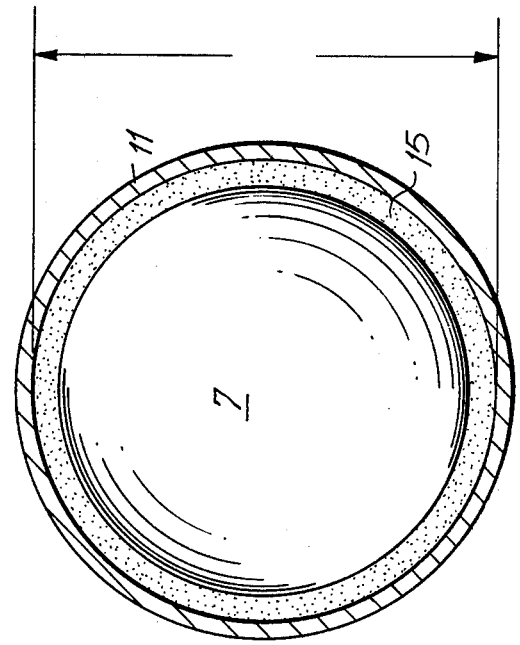
FIG. 5 is an enlarged partial cross sectional view of FIG. 4 taken along line 5—5 of FIG. 4.

The filling operation for preparing the products of this invention are best seen in connection with FIG. 4. After the alkaline tablets are formed, they are fed to a filling station 9 where each is inserted into the body 11 of a capsule and the capsule containing the alkaline tablet is passed on to a second station 13 where it receives the powdered aspirin mixture 15. After receiving the powdered aspirin mixture, the capsule is capped with the upper half 17 of the capsule and the product is completed.

The capsules that are employed in the present invention may be conventional gelatin capsules that are well known to those skilled in this art. These may vary somewhat in size but usually they will be #0, #1, #2 and #3. Since a fast rate of absorption of aspirin into the bloodstream is a desirable feature, it is advantageous to employ a capsule which in itself is fast dissolving. With this in mind, it is useful to include in the gelatin material that constitutes the capsule about 10% by weight of calcium carbonate based on the total weight of the capsule mentioned.

The number of capsules of this invention that will be given as a single dose may vary with amount of active ingredient contained in the capsule, the age of the subject or the results desired. In the usual cases, one or two capsules are ordinarily adequate.

The capsule products of this invention may be employed in treating those conditions for which aspirin is generally prescribed. This will ordinarily be to relieve pain and/or to reduce a fever in the subject. The one or two capsule doses mentioned may be used to bring about these results.

The following Examples are given to further illustrate this invention. It is to be understood, however, that the invention is not limited thereto.

EXAMPLE 1

Formula CL 1565-83A

| Dosage Unit Amt. mg/cap. | Item No. | Ingredients | Quan. for 120,000 capsules in gms. |
|---|---|---|---|
| Part I Alkaline Tablet: | | | |
| 23.90 | 1 | Magnesium carbonate | 2868 |
| 95.60 | 2 | Calcium carbonate | 11473.0 |
| 38.24 | 3 | Magnesium oxide | 4588.8 |
| 2.87 | 4(a) | Starch (internal) | 2294.4 |
| 16.25 | 4(b) | Starch (external) | |
| | 5 | Deionized water or distilled water | (1000 ml) |
| 176.86 | | | |
| 0.35 | 6 | Magnesium stearate | 42.0 |
| 177.21 mg. | | | 21266.2 |
| Part II Aspirin Mixture: | | | |
| 20.00 Range(10–30) | 7 | Modified starch 1500 - Sta-Rx 1500 (dried) | 2400. |

-continued

| Dosage Unit Amt. mg/cap. | Item No. | Ingredients | Quan. for 120,000 capsules in gms. |
|---|---|---|---|
| 2.00 Range (2-5) | 8 | Dimethylpolysiloxane Fluid 360 Medical Type 350 Centistokes | 240. |
| 0.20 | 9 | Polyoxyethylene(20) sorbitan monooleate (Tween 80) | 24. |
| 500.00 | 10 | Aspirin, 80 mesh | 60,000 |
| 522.20 | | | 62,664. |

Procedure:

A. Alkaline Granulation
 (a) To a ribbon blender, charge 1, 2 and 3 i.e. magnesium carbonate, magnesium oxide and calcium carbonate;
 (b) add internal starch (4a) to boiling water (100° C.) to hydrolyze the starch;
 (c) add (b) to (a) and mix thoroughly;
 (d) add remaining starch (external 4b) to (c) and mix for 5 minutes;
 (e) pass (d) through a Tornado Mill with a ¾" screen;
 (f) dry (e) in a Fluid Bed Drier to a moisture content of from 1-3% maximum;
 (g) pass dried granulation (f) through an oscillator with a 12 mesh screen; and
 (h) add 6 (magnesium stearate) and mix in a V-blender.

B. Alkaline Tablet
 Compress above granulation on a special 7/32" spherical punch to a weight of 177.2 mg and a thickness of 0.225" and a diagonal measurement of 0.245±0.005. Disintegration time for this tablet is 10-30 sec.

C. Aspirin Mixture
 To a ribbon blender charge 10 (aspirin) and 7 (dried Sta-Rx). Combine 8 and 9 (i.e. silicone fluid and Tween 80) and spray onto the mixture of aspirin and Sta-Rx; mix 10 minutes.

D. Finished Capsule Product
 Using a semi-automatic (i.e. Elanco 85) or high speed automatic capsule filler (i.e. H&K 1200) insert 1 compressed alkaline tablet into an empty opened #0 gelatin capsule using a feeding device. Then add required amount of aspirin mixture (522.2 mg) and close capsule with its cap.

Acid Consuming Capacity Test

Alkaline pellets prepared in accordance with Example 1 (CL 1565-83A) were reacted with 0.1 NHCl in a typical fashion to measure the total acid consuming capacity (ACC). The value was determined to be 4.3 meq±0.2 compared to a theoretical value of 4.3 meq. In contrast, a similar sized pellet (190 mg) comprised of 50 mg. magnesium carbonate and 120 mg calcium carbonate has an ACC value of only 3.4 meq measured in the same way.

Although the invention has been described with reference to specific forms thereof, it will be understood that many changes and modifications may be made without departing from the spirit of this invention.

What is claimed is:

1. As a unit dosage form a capsule having incorporated therein at least one alkaline tablet and an aspirin mixture; said aspirin mixture being present in said capsule as a powder or granulated material; said alkaline tablet comprising a combination of calcium carbonate, magnesium carbonate and a magnesium oxy component selected from the group consisting of magnesium oxide, magnesium hydroxide and a mixture of magnesium oxide and magnesium hydroxide; the aspirin being present in said capsule at a level of from 325 mg. to about 650 mg.; said capsule being dimensioned so that it may be conveniently swallowed and at the same time is not too small to accomodate effective amounts of capsule ingredients; said alkaline tablet being dimensioned so as to conveniently fit into said capsule; said powder or granulated material being essentially free of antacid and said alkaline tablet being essentially free of aspirin.

2. A unit dosage form according to claim 1 wherein the quantity of alkaline material contained in the capsule is between about 20% to about 150% by weight based on the total weight of aspirin contained in the capsule.

3. A unit dosage form according to claim 2 in which said alkaline material, based on the weight of aspirin in the capsule comprises:
 (a) from about 5% to about 20% calcium carbonate;
 (b) from about 2% to about 10% magnesium carbonate; and
 (c) from about 2% to about 20% magnesium oxy component.

4. A unit dosage form according to claim 1 in which said aspirin is present in said capsule at a level in the range of from about 400 mg to about 650 mg.

5. A unit dosage form according to claim 4 in which the quantity of alkaline material contained in the capsule is between about 20% to about 150% by weight based on the total weight of the aspirin in said capsule.

6. A unit dosage form according to claim 5 in which said alkaline material based on the weight of aspirin in the capsule comprises:
 (a) from about 5% to about 20% calcium carbonate;
 (b) from about 2% to about 10% magnesium carbonate; and
 (c) from about 2% to about 20% magnesium oxy component.

7. A unit dosage form according to claim 6 in which said magnesium oxy component is magnesium oxide.

8. A unit dosage form according to claim 6 in which said magnesium oxy component is magnesium hydroxide.

9. A unit doage form according to claim 6 in which said magnesium oxy component is a mixture of magnesium oxide and magnesium hydroxide.

10. A unit dosage form according to claims 1, 2, 3, 4, 5, 6, 7, 8 or 9 in which the aspirin is contained in said capsule at a level of about 500 mg.

11. A unit dosage form according to claim 1 in which at least one additional pharmaceutically active ingredient is contained in said capsule.

12. A unit dosage form according to claim 11 in which said additional pharmaceutically active ingredient is an additional analgesic.

13. A unit dosage form according to claim 11 in which said additional pharmaceutically active ingredient is a decongestant.

14. A unit dosage form according to claim 11 in which said additional pharmaceutically active ingredient is an antihistamine.

15. A unit dosage form according to claim 11 in which said additional active ingredients is a mixture of decongestant, antihistamine and antitussive.

16. A method for alleviating pain and/or fever in a subject which comprises administering to said subject sufficient unit dosage forms defined in claims 1, 2, 3, 4, 5, 6, 7, 8, or 9 to alleviate said pain and/or fever.

* * * * *